United States Patent

Katafuchi

[11] Patent Number: 5,980,829
[45] Date of Patent: Nov. 9, 1999

[54] NEUTRALIZATION TESTING APPARATUS

[75] Inventor: Tadashi Katafuchi, Ichihara, Japan

[73] Assignee: Idemitsu Kosan Co., Ltd., Tokyo, Japan

[21] Appl. No.: 08/944,787

[22] Filed: Oct. 6, 1997

[30] Foreign Application Priority Data

Oct. 29, 1996 [JP] Japan ................................. 8-286551

[51] Int. Cl.$^6$ ................................................. G01N 31/16
[52] U.S. Cl. ..................... 422/75; 422/82.12; 422/82.13; 436/61; 436/147; 436/148; 436/163
[58] Field of Search ........................... 73/864.86, 864.87; 422/75, 80, 82.12, 82.13; 436/60, 61, 147, 148, 163

[56] References Cited

U.S. PATENT DOCUMENTS 3,578,404  5/1971  Walles et al. .
3,660,035  5/1972  Marsh .
3,915,636  10/1975  Ford, Jr. et al. .
4,088,447  5/1978  Walker .
5,300,207  4/1994  Dahms .

Primary Examiner—Jan Ludlow
Attorney, Agent, or Firm—Oblon, Spivak, McClelland, Maier & Neustadt, P.C.

[57] ABSTRACT

A neutralization testing apparatus and a neutralization testing method which allow a neutralization reaction rate of a liquid sample such as lubricant oil to be accurately measured are provided. Reagent injecting device for injecting a reagent which neutralizes the liquid sample is provided on a lid member of a closed container into which the liquid sample is charged. The reagent injecting device is an acid injecting port which penetrates through the closed container and an air-tight sealing member which closes the acid injecting port and which permits an injector needle for injecting the reagent to penetrate therethrough. Because no gas leakage occurs even when the injector needle is penetrated because of the elasticity of the air-tight sealing member, the measuring conditions within the closed container do not change and the neutralization reaction rate may be found accurately.

4 Claims, 4 Drawing Sheets

NEUTRALIZATION TESTING APPARATUS

BACKGROUND OF THE INVENTION

1. Field of the Invention

The present invention relates to a neutralization testing apparatus and a neutralization testing method of a liquid sample such as lubricant oil and may be utilized in measuring an acid neutralization rate of cylinder oil which is heavy lubricant oil for example.

2. Description of Related Art

Hitherto, lubrication by means of fats and oils has been used frequently in a driving mechanism such as an engine. For instance, cylinder oil for smoothly driving a piston within an engine cylinder is used in a ship engine, beside system oil used for smoothly actuating the driving mechanism.

In addition to the performance of smoothly driving the piston within a high temperature and high pressure atmosphere within the cylinder, such cylinder oil is required to have a performance of neutralizing corrosive sulfur compound which is produced within the cylinder along the combustion of fuel oil to prevent the cylinder and piston from corroding.

Accordingly, it is an important factor to find an acid neutralization rate as the performance of the cylinder oil in developing the cylinder oil. Therefore, the performance of the cylinder oil has been evaluated by finding the neutralization reaction rate of the cylinder oil by using an acid neutralization testing apparatus since the past.

As the acid neutralization testing apparatus of the cylinder oil, a testing apparatus for finding a neutralization reaction time of sulfuric acid and the cylinder oil and for finding the acid neutralization rate from that by charging the cylinder oil which is a liquid sample into a closed container whose internal temperature and pressure are kept constant, by injecting the sulfuric acid to the closed container by an injector via a reagent injecting port which is in communication with the inside of the closed container and by measuring changes in pressure within the closed container.

In such an acid neutralization testing apparatus, there has been provided an air-tight valve at the reagent injecting port and the sulfuric acid has been injected through a series of works of (1) opening the valve, (2) inserting the injector needle to inject the sulfuric acid, and (3) closing the valve.

Then, the time when the valve is closed has been set as a neutralization reaction starting time of the cylinder oil and the acid neutralization rate of the cylinder oil has been found from the elapsed change in the increase of pressure within the testing apparatus after that.

However, there has been a problem that the neutralization reaction rate cannot be found accurately when the measurement is carried out by means of the above-mentioned acid neutralization testing apparatus in a high temperature range in which the reaction takes place quickly because gas leaks as the valve is opened and the measuring conditions within the closed container change.

Further, it has been difficult to set the measuring conditions of the high temperature and high pressure atmosphere like that in an actual cylinder by the prior art acid neutralization testing apparatus.

Due to that, there has been a problem that the cylinder oil cannot be measured directly because the cylinder oil which is highly viscous in a normal temperature has to be diluted in measuring it.

Further, when the time when the valve is closed is set as the neutralization reaction starting time as described above, a time lag is produced between that time and the actual neutralization starting time when the sulfuric acid contacts with the cylinder oil. Therefore, there has been a problem that the neutralization reaction time until when the reaction ends cannot be found accurately and the neutralization reaction rate cannot be found accurately.

Accordingly, the present invention has been devised in order to solve the aforementioned problems by providing a neutralization testing apparatus and a neutralization testing method which allow the neutralization reaction rate of a liquid sample such as lubricant oil to be measured accurately.

SUMMARY OF THE INVENTION

A neutralization testing apparatus of the present invention comprises a closed container into which a liquid sample is charged; reagent injecting means for injecting a reagent which neutralizes the liquid sample into the closed container; temperature detecting means, provided within the closed container to contact with the liquid sample, for determining an increase of temperature of the liquid sample due to neutralization; and pressure detecting means, provided within the closed container, for determining changes in pressure within the closed container caused by the neutralization; and a neutralization rate of the liquid sample is found by measuring the changes in temperature of the liquid sample and the changes in pressure within the closed container along the elapse of time by these detecting means. The neutralization testing apparatus is characterized in that the reagent injecting means comprises a reagent injecting port created through the closed container so as to penetrate therethrough and an air-tight sealing member for closing the reagent injecting port and keeping the inside of the closed container air-tight; and the air-tight sealing member permits an injector needle for injecting the reagent to penetrate therethrough.

Here, the liquid sample may be a liquid substance such as petroleum products, mineral oils other than petroleum, and chemical compounds and includes also solid and semi-solid fats and oils in normal temperature. For instance, cylinder oil which is one of heavy lubricant oils and is highly viscous in normal temperature may be also included in the liquid sample here. In short, a substance which is liquidized under the measuring conditions such as the temperature and pressure within the closed container may be the liquid sample here.

The air-tight sealing member includes a member made of a soft synthetic resin, beside a member made of an elastomeric material such as natural rubber and synthetic rubber. It includes not only non-foamed solid substance but also those whose form is a foamed substance such as urethane foam. It is noted that a closed cell type foamed substance is preferable from the aspect of maintaining the air-tightness.

In short, the material of the air-tight sealing member may be determined appropriately in accordance to the required operational performance such as the diameter of the injector needle which penetrates through that and the atmosphere within the closed container.

The temperature detecting means may be a thermometer or a thermocouple for example which can detect a thermal change such as temperature or a quantity of heat caused by the reaction.

The pressure detecting means may be one of various known pressure sensors as long as it can detect changes in pressure.

According to the present invention described above, the reagent may be injected by penetrating the injector needle for injecting the reagent through the air-tight sealing means, so that the air-tight state within the closed container is maintained and no change occurs in the measuring conditions regardless of the injecting operation. Accordingly, the neutralization reaction rate may be found accurately.

In the invention described above, it is preferable to adopt a pressure-proof container which can sustain a high temperature and high pressure atmosphere as the closed container. It is particularly preferable to adopt a pressure-proof container which can sustain and can be used under pressure of around 1 MPa.

That is, because the use of the pressure-proof container as the closed container allows the conditions within the closed container to be set at the condition of high temperature and high pressure atmosphere, it becomes possible to measure cylinder oil by directly charging it into the closed container and the neutralization reaction rate can be found in the state close to the actual use conditions.

Further, it is preferable to provide a heater on the closed container to prevent it from dewing. That is, the provision of the heater allows to prevent it from dewing, which otherwise occurs on the inner surface of the closed container above the liquid level of the liquid sample, thus allowing the neutralization reaction rate to be found more accurately. The heater may be suitably provided at the position described latter in the description of the embodiment.

Preferably, a temperature detecting region of temperature control means is disposed at the position contacting with the liquid sample together with the temperature detecting region of temperature detecting means. It is particularly preferable to dispose the temperature detecting region of the temperature detecting means at the position close to the liquid level of the liquid sample. It is because the injection of the reagent which neutralizes the liquid sample is detected more quickly by disposing the temperature detecting region of the temperature detecting means at the position close to the liquid level of the liquid sample.

A neutralization testing method of the present invention has a closed container into which a liquid sample such as lubricant oil is charged; a reagent injecting port which is created in communication with the inside of the closed container for injecting a reagent which neutralizes the liquid sample by an injector, air-tight means for closing the reagent injecting port and keeping the inside of the closed container air-tight, temperature detecting means, provided within the closed container in contact with the liquid sample, for determining an increase of temperature of the liquid sample due to neutralization; and pressure detecting means, provided within the closed container, for determining changes in pressure within the closed container caused by the neutralization; to find a neutralization rate of the liquid sample by measuring the changes in temperature of the liquid sample and the changes in pressure within the closed container along the elapse of time by these detecting means. The neutralization testing method is characterized in that the time when the change in temperature of the liquid sample is determined by the temperature detecting means after injecting the reagent is set as a neutralization reaction starting time of the liquid sample.

The present invention described above allows the change in temperature such as an increase of temperature caused by neutralization heat of the reagent and the liquid sample may be immediately determined by the temperature detecting means, so that the neutralization reaction rate of the liquid sample may be found accurately.

The inventive neutralization testing method may be suitably adopted in a method using lubricant oil as the liquid sample and sulfuric acid as the reagent. The inventive neutralization testing method may be also suitably carried out as a neutralization testing method of non-diluted lubricant oil or non-diluted cylinder oil in particular by adopting the pressure-proof container as the closed container.

The specific nature of the invention, as well as other objects, uses and advantages thereof, will clearly appear from the following description and from the accompanying drawings.

DESCRIPTION OF PREFERRED EMBODIMENT

A preferred embodiment of the present invention will be explained below with reference to the drawings.

Figure 1:
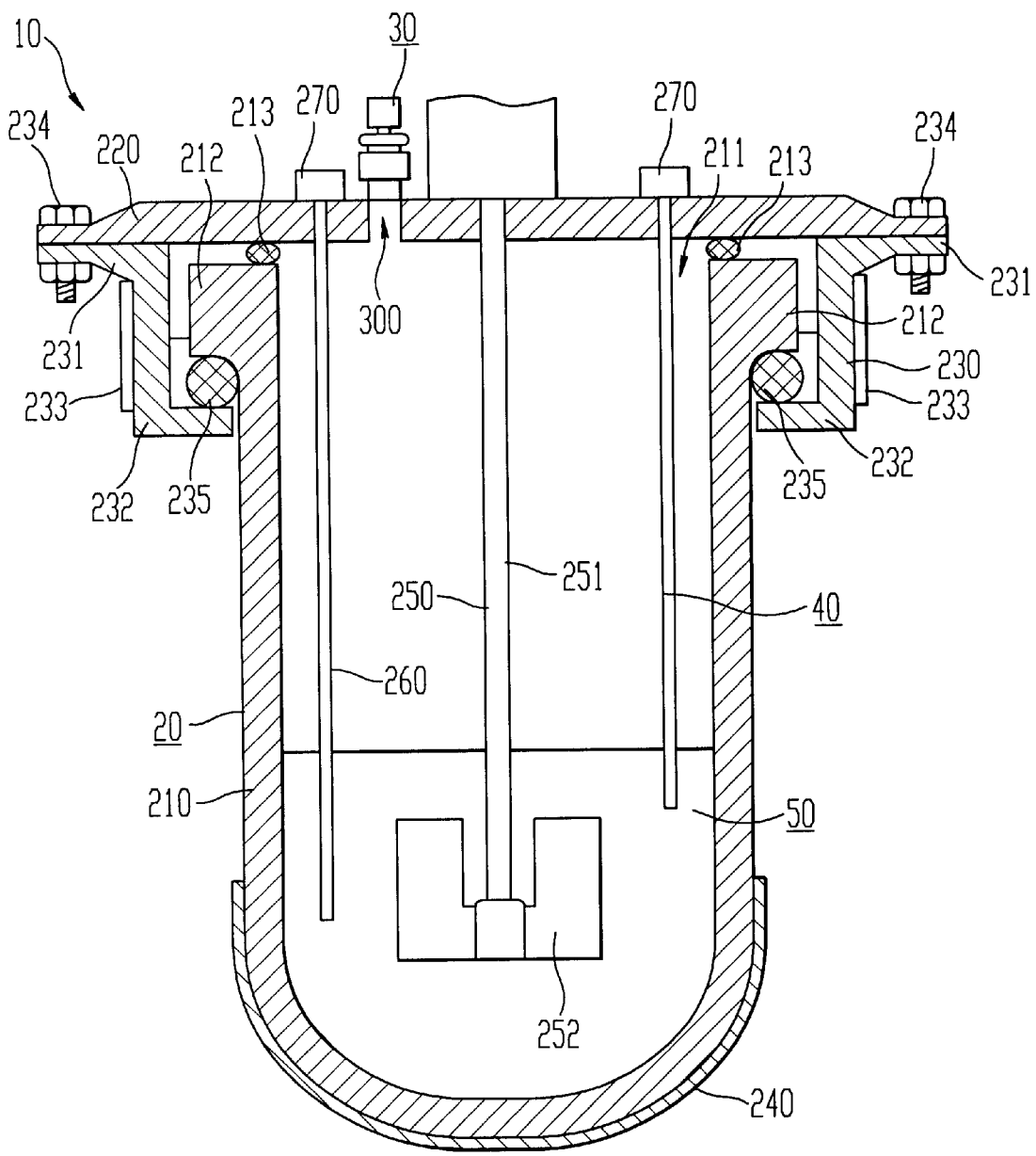
FIG. 1 is a section view showing an internal structure of a neutralization testing apparatus according to a preferred embodiment of the present invention.

FIG. 1 shows an internal structure of a neutralization testing apparatus according to the embodiment of the present invention. The neutralization testing apparatus (acid neutralization testing apparatus) 10 comprises a closed container 20, acid injecting means 30 which is reagent injecting means provided at the upper part of the closed container 20 and an acid injection detecting thermocouple 40 which is temperature detecting means provided within the closed container 20. Cylinder oil 50 which is a liquid sample is charged into the closed container 20.

The closed container 20 also comprises a main body 210 of the container into which the cylinder oil is charged, a lid member 220 for closing the main body 210 to keep it air-tight, and a frame member 230 provided so as to surround the main body 210 and directly joined with the lid member 220.

Here, the lid member 220 and the frame member 230 are made of cast iron and the main body 210 is made of monolithic pressure-proof glass. The closed container 20 is made to be a pressure-proof container which can sustain up to 1 MPa by hermetically joining these members.

The main body 210 is approximately a cylindrical member whose bottom is closed semi-spherically and in which an opening face 211 is created at the upper part thereof. A projection 212 which projects radially toward the outside of the cylinder is formed at the outer periphery of the opening face 211.

A heater 240 for controlling the temperature of the liquid sample is provided at the outer peripheral surface near the bottom of the main body 210.

The lid member 220 is a disk-like member for covering the opening face 211 of the main body 210. The lid member 220 is provided with an agitator 250 for agitating the cylinder oil 50 and an oil temperature controlling thermocouple 260 for controlling the temperature of the cylinder oil 50, beside the acid injecting means 30 described later and the, acid injection detecting thermocouple 40.

The frame member 230 is approximately a cylindrical member which covers the outer surface of the main body 210 and is opened at the top and bottom thereof. It is attached to the main body 210 so as to be vertically movable in FIG. 1.

The frame member 230 is also provided with an outward projection 231 formed radially toward the outside of the cylinder at the opening face at the upper side thereof and an inward projection 232 which projects radially toward the inside of the cylinder. A heater 233 for preventing dewing is provided also at the cylindrical outer surface of the frame member 230.

The main body 210 is joined with the lid member 220 through the intermediary of the frame member 230. The lid member 220 is joined with the frame member 230 near the outer peripheral edge thereof by bolts 234 and the frame member 230 is abutted and joined with the main body 210 through the intermediary of a cushion 235 at the upper face of the inward projection 232 and the lower face of the projection 212 of the main body 210.

An O-ring 213 is also interposed between the opening face 211 of the main body 210 and the lower face of the lid member 220. When the bolts 234 are tightened, the cushion 235 and the O-ring 213 are compressed and deformed, thus maintaining the air-tightness of the closed container 20.

It is noted that although not shown in FIG. 1, a pressure sensor for determining an increase of pressure within the system is provided as pressure detecting means within the closed container 20 and is connected to an outside pressure sensor monitor in order to measure the pressure within the closed container 20.

The acid injection detecting thermocouple 40 is provided on the side of the lower face of the lid member 220 in FIG. 1 and is extended downward together with the agitator 250 and the oil temperature controlling thermocouple 260.

The acid injection detecting thermocouple 40 and the oil temperature controlling thermocouple 260 are provided such that the edge portions thereof which are temperature detecting sections reach under the liquid level of the cylinder oil 50 and the cardinal ends thereof penetrate through the lid member 220 and are connected to the outside temperature detector 270. It is noted that the edge portion of the acid injection detecting thermocouple 40 is disposed at the region close to the liquid level of the cylinder oil 50 as compared to the edge portion of the oil temperature controlling thermocouple 260.

The agitator 250 comprises a shaft 251 and a propeller 252 created at the edge of the shaft 251 and is provided so as to be rotatable centering on the axis which extends almost from the center of the circular lid member 220. The cardinal end of the shaft 251 penetrates through the lid member 220 and is connected with a motor (not shown in FIG. 1) provided at the outside. It is noted that although not shown in FIG. 1, no gas leaks from the parts where they penetrate through the lid member 220 because air-tight seal is applied and the air-tightness within the closed container 20 is kept.

Figure 2:
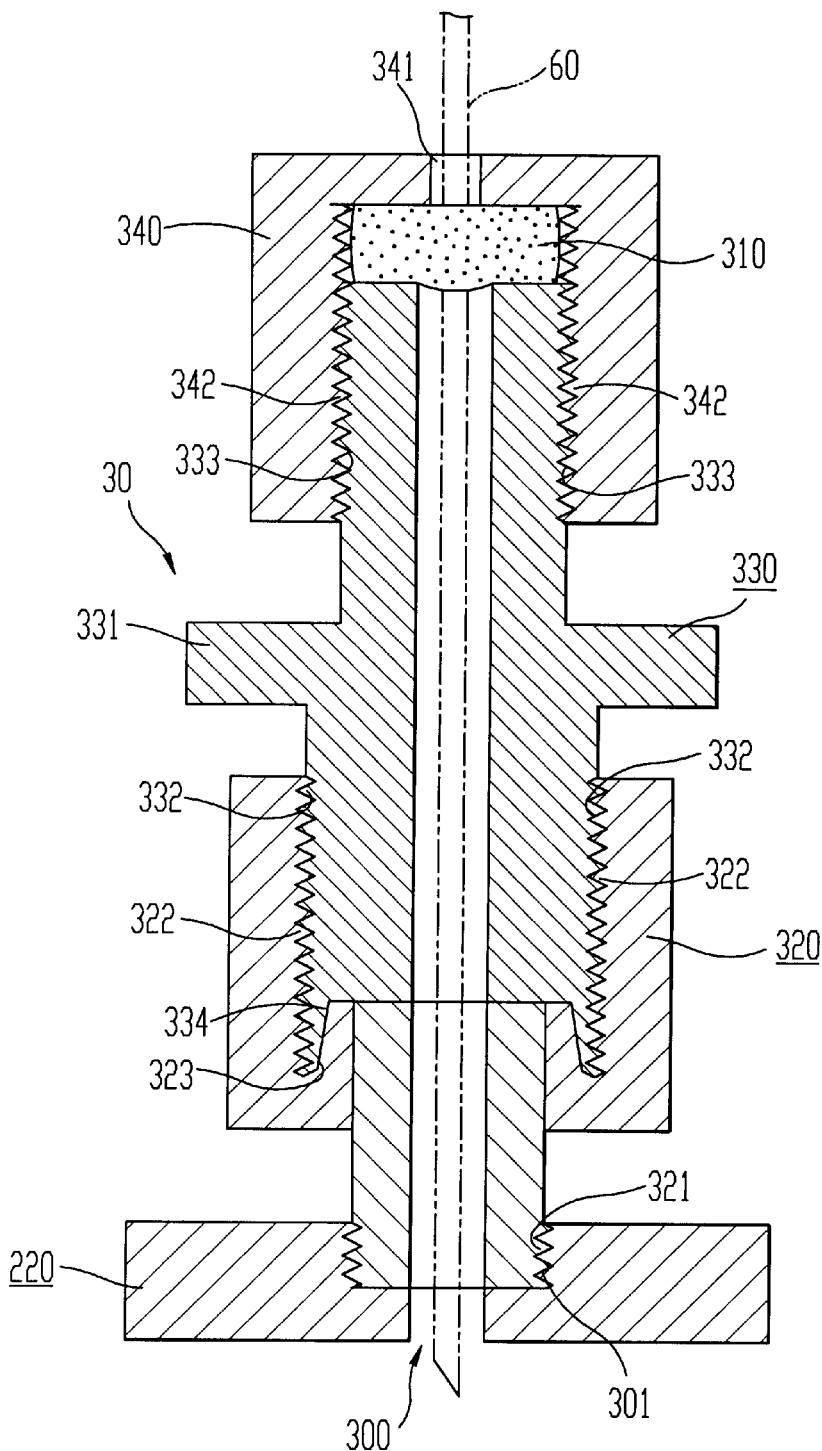
FIG. 2 is a section view showing a structure of reagent injecting means in the testing apparatus of the above-mentioned embodiment.
Figure 3:
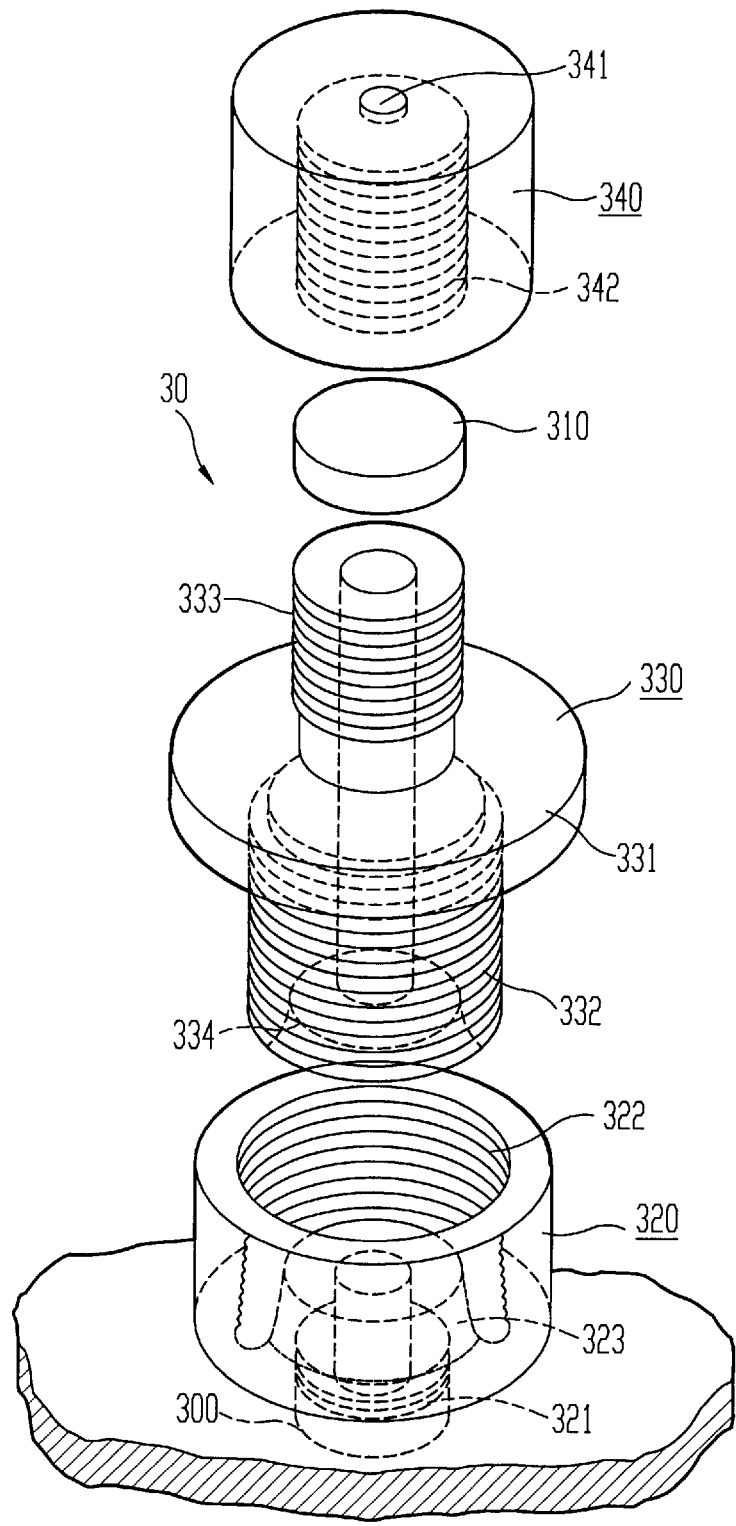
FIG. 3 is an exploded perspective view of the reagent injecting means in the testing apparatus of the above-mentioned embodiment.

As shown in a section view in FIG. 2 and an exploded perspective view in FIG. 3, the acid injecting means 30 is provided on the above-mentioned lid member 220.

The acid injecting means 30 has an acid injecting port 300 which penetrates through the lid member 220 and a disk-like rubber plug 310 which is an air-tight sealing member. Beside them, it comprises a joint member 320 which is jointed with the acid injecting port 300, a guide member 330 jointed with the joint member 320 for guiding an injection needle 60 to the acid injecting port 300 and a fixed member 340 which is jointed with the guide member 330 for fixing the rubber plug 310 on the guide member 330.

The acid injecting port 300 is created on the lid member 220 so as to penetrate through the closed container 20. In correspondence to the acid injecting port 300, a female screw section 301 is formed at the upper face of the lid member 220 in FIG. 1 so as to joint with the joint member 320.

The rubber plug 310 is nearly a disk-like member which is made of silicon rubber having no gas permeability from the surface to the back thereof. Even if a small hole which penetrates from the surface to the back of the plug is created, it is closed by the elasticity of the silicon rubber and the air-tightness of the rubber plug 310 is kept.

As it is apparent from FIGS. 2 and 3, the joint member 320 is a member having a shape in which cylinders having different diameters at the top and bottom are jointed. It has a male screw section 321 formed on the outer face of the lower cylinder having a small diameter and a female screw section 322 formed on the inner face of the upper cylinder having a large diameter. A tapered convex portion 323 is provided at the bottom of the female screw section 322 along the direction in which the cylinder is extended. Then, the joint member 320 is joined with the acid injecting port 300 by screwing the male screw section 321 into the female screw section 301 of the acid injecting port 300.

The guide member 330 is approximately a cylindrical member whose both ends are opened and is provided with, as seen in FIG. 2, a flange-like handle 331 formed at the middle section of the guide member 330 so as to project radially toward the outside, a male screw section 332 formed at the lower part of the outer face of the cylinder and a male screw section 333 formed at the upper part thereof. Further, an inversely tapered concave section 334 is formed at the end face of the lower part of the guide member 330 in FIG. 2 along the outer periphery of the radial end face of the cylinder.

Then, the male screw section 332 of the guide member 330 is screwed into the female screw section 322 of the joint member 320 to joint the guide member 330 with the joint member 320 and to joint the convex portion 323 of the joint member 320 hermetically with the concave portion 334 of the guide member 330 through an intermediary of a seal tape (not shown in FIGS. 2 and 3).

The fixed member 340 is a cylindrical member whose upper end is closed and whose lower end is opened as shown in FIG. 2. An insertion hole 341 is created through the upper end thereof to insert the injector needle 60 and a female screw section 342 is formed on the inner face of the cylinder.

Then, the rubber plug 310 is held within the cylinder of the fixed member 340. When the female screw section 342 of the fixed member 340 is screwed with the male screw section 333 at the upper part of the guide member 330, the rubber plug 310 is compressed and fixed between the closed end of the fixed member 340 and the upper face of the guide member 330.

An acid neutralization reaction rate of the cylinder oil 50 may be measured by the neutralization testing apparatus 10 described above through the following procedure.

At first, the cylinder oil 50 is charged into the main body 210 and then the inside of the closed container 20 is put into the air-tight state by the lid member 220.

Then, the temperature of the cylinder oil 50 is increased by using the agitator 250 and the heaters 240 and 233 together as necessary to control the measuring conditions within the closed container 20 to the preset values while determining the temperature by the temperature sensor 270 to which the oil temperature controlling thermocouple 260 is connected.

Next, sulfuric acid which neutralizes the cylinder oil 50 is put into the injector in advance and the injector needle 60 is inserted to the inside of the closed container 20 by penetrating through the rubber plug 310 from a hole 341 created through the fixed member 340 which composes the acid injecting means 30 to inject a predetermined amount of sulfuric acid to the closed container 20.

Immediately after the injection, a change in temperature of the cylinder oil 50 is determined by the temperature detector 270 to which the acid injection detecting thermocouple 40 is connected to record the time when the change in temperature is determined as a starting time of the acid neutralization reaction.

Then, after determining the reaction starting time, the increase of pressure within the closed container 20 is measured along an elapse of time by the aforementioned pressure sensor monitor and a point of time when the pressure within the closed container 20 becomes constant is recorded as a neutralization reaction ending time.

It is noted that the pressure increases within the closed container 20 due to carbon dioxide gas which is produced along the neutralization reaction between the cylinder oil 50 which is the liquid sample and the sulfuric acid which is the reagent.

The above-mentioned embodiment brings about the following effects.

Because the rubber plug 310 is used in the acid injecting means 30, the hole caused by the injector needle 60 is closed by the elasticity of the rubber plug 310 even when the injector needle 60 penetrates through the rubber plug 310. Accordingly, the air-tight state within the closed container 20 may be maintained and the neutralization reaction rate may be measured accurately without causing any error in the measuring conditions due to leakage of gas and the like.

Further, because the rubber plug 310 is attached in the state compressed by the guide member 330 and the fixed member 340, the force of closing the hole caused by the injector needle 60 by the elasticity of the rubber plug 310 is also large, so that the air-tight state may be maintained even if the pressure within the closed container 20 is high.

Further, because the measuring conditions within the closed container 20 may be set at high temperature and high pressure conditions which are close to those of the inside of an actual cylinder by constructing the closed container 20 so as to be able to sustain up to 1 MPa of internal pressure, the acid neutralization reaction rate which is closer to the actual condition may be found.

Still more, the neutralization reaction rate may be found in a state in which the cylinder oil 50 can be reacted (agitated) more easily by reducing the viscosity of the cylinder oil 50 by keeping the inside of the closed container 20 at high temperature. Accordingly, the neutralization reaction rate may be found accurately without diluting the cylinder oil 50 with base oil.

Further, because a time lag with the actual neutralization reaction starting time may be mostly eliminated by setting the time when the temperature as determined by the acid injection detecting thermocouple 40 changes as the neutralization reaction starting time. In Particular, the reaction with the sulfuric acid which is injected from the upper part of the closed container 20 may be quickly detected by disposing the edge of the acid injection detecting thermocouple 40 near the liquid level of the cylinder oil 50, the neutralization reaction rate may be found accurately also from this point of view.

Next, results on experiments carried out to compare the performance of the inventive neutralization testing apparatus and the neutralization testing method with that of the prior art acid neutralization testing apparatus and the neutralization testing method will be described below.

The above-mentioned neutralization testing apparatus 10 was used as the inventive neutralization testing apparatus and the above-mentioned procedure was adopted as the neutralization testing method.

Meanwhile, as the prior art acid neutralization testing apparatus, an apparatus comprising a container equipped with a pressure sensor, a thermometer and an air-tight valve (sulfuric acid injecting port) was used as a closed container and means which can set the temperature of cylinder oil charged into this container at a predetermined temperature was adopted.

The acid neutralization test was carried out as follows. That is, the cylinder oil was charged into the closed container and was heated. When the temperature reached at a predetermined temperature, the air-tight valve was opened to inject the sulfuric acid by inserting an injector needle. Then, after closing the valve, a neutralization reaction rate was found by recording changes in temperature within the reaction system and changes in pressure within the closed container along the elapse of time along the elapse of time.

The composition of the liquid sample (cylinder oil) used for the comparison of the performance was as follows:

| | |
|---|---|
| base oil | 75.5 wt % |
| alkenil succinic acid imide | 0.5 wt % |
| TBN 280 sulfonate | 24.0 wt % |

Further, in the comparison of the performance, the time up to when the increase of the pressure within the closed container was detected after injecting the sulfuric acid and the pressure within the closed container after 30 seconds from the injection of the sulfuric acid were measured as characteristic values. Table 1 shows the measuring conditions.

TABLE 1

| Items | Measuring Conditions |
|---|---|
| Oil Temperature (° C.) | 160 |
| Concentration of sulfuric acid (N) | 35.9 |
| Amount of sulfuric acid added(ml/liquid sample 100 g) | 1 |

Table 2 shows the measurement results.

TABLE 2

| | Pressure increase starting time | Pressure within closed container after 30 seconds |
|---|---|---|
| Embodiment | 0 second | 1.4 kg/cm$^2$ |
| Comparative Case | 43 seconds | 0 kg/cm$^2$ |

Thus, the neutralization testing apparatus 10 of the present embodiment allows the starting time of the acid neutralization reaction to be accurately grasped as the pressure increase starting time and the neutralization reaction rate of the cylinder oil to be accurately found. Further, because the air-tightness of the closed container 20 is kept even during the measurement, the measuring conditions within the closed container 20 do not change due to leakage of gas and the like and the neutralization reaction rate may be found accurately.

It is noted that the present invention is not confined only to the above-mentioned embodiment but contains also the following variations.

Figure 4:
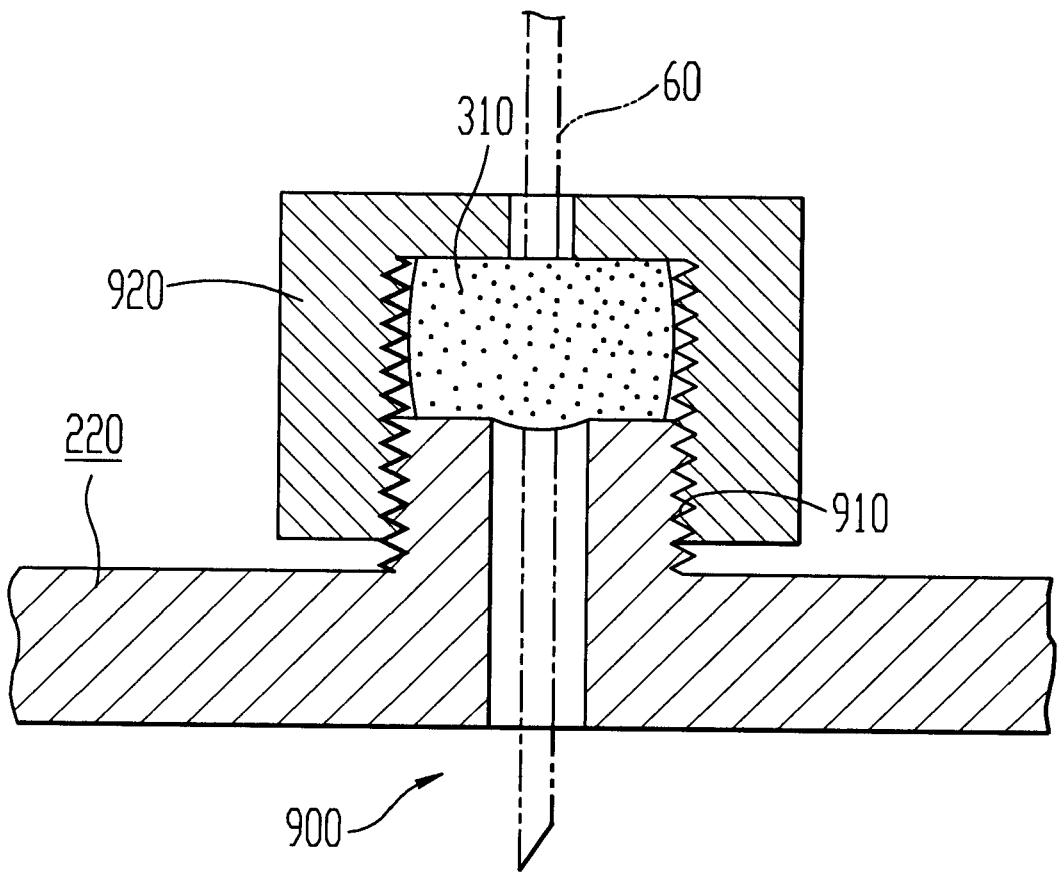
FIG. 4 is a section view showing reagent injecting means which is a modification of the reagent injecting means of the above-mentioned embodiment.

That is, although the reagent injecting means (acid injecting means) 30 has been composed of the reagent injecting port (acid injecting port) 300, the rubber plug 310, the joint member 320, the guide member 330 and the fixed member 340 in the embodiment described above, reagent injecting means 90 as shown in FIG. 4 may be also adopted.

The reagent injecting means 90 shown in FIG. 4 has an acid injecting port 900 and the rubber plug 310. A male screw section 910 is formed so as to protrude outside at the reagent injecting port 900 and a fixing member 920 is screwed with the male screw section 910 so as to pinch and fix the rubber plug 310.

In short, any structure may be adopted so long as it allows the rubber plug to be fixed at the reagent injecting port and the injector needle to be penetrated therethrough without causing any gas leakage even when the pressure within the closed container increases.

Further, although the acid neutralization test has been carried out by using the cylinder oil 50 for ship engine as the liquid sample in the embodiment described above, engine oil for automobiles and other lubricant oils may be measured by the same method. The same test may be also carried out by melting a semi-solid substance such as grease as a liquid sample.

Still more, although the neutralization reaction test has been carried out by using the sulfuric acid as the reagent in the embodiment described above, the inventive neutralization testing apparatus and neutralization testing method may be used also in a neutralization reaction test using a basic reagent such as sodium hydroxide.

Beside those described above, the concrete structure, shape and others of the present invention in implementing it may be modified within the scope of achieving the object of the present invention.

Thus, the inventive neutralization testing apparatus and neutralization testing method described above allow the neutralization reaction starting time to be accurately detected without causing any change in the measuring conditions due to gas leakage or the like, so that the neutralization reaction of the liquid sample may be measured accurately.

What is claimed is:

1. A neutralization testing apparatus, comprising:

a closed container into which a liquid sample is charged;

reagent injecting means for injecting a reagent which neutralizes said liquid sample into said closed container;

temperature detecting means, provided within said closed container to contact with said liquid sample, for determining an increase of temperature of said liquid sample due to neutralization; and pressure detecting means, provided within said closed container, for determining changes in pressure within said closed container caused by the neutralization;

means for determining a neutralization rate of said liquid sample found by measuring the changes in temperature of said liquid sample and the changes in pressure within said closed container along the elapse of time by said temperature and pressure detecting means;

said neutralization testing apparatus being characterized in that:

said reagent injecting means comprises a reagent injecting port created through a wall of said closed container so as to penetrate therethrough and an air-tight sealing member for closing said reagent injecting port and keeping the inside of said closed container air-tight; and said air-tight sealing member permits an injector needle for injecting said reagent to penetrate therethrough.

2. The neutralization testing apparatus according to claim 1, wherein said closed container is a pressure-proof container.

3. The neutralization testing apparatus according to claim 1 or 2, wherein a heater for preventing dewing is provided on said closed container.

4. The neutralization testing apparatus according to claim 1 or 2, further comprising temperature detecting means which is provided within said closed container to contact with said liquid sample to control the temperature of said liquid sample;

a temperature detecting region of said temperature detecting means for determining the increase of temperature due to the neutralization being located at the position close to the liquid level of said liquid sample as compared to a temperature detecting region of said temperature detecting means for controlling the temperature.

* * * * *